United States Patent [19]
Philpot, Jr.

[11] 4,083,363
[45] Apr. 11, 1978

[54] BLOOD VISCOSITY DETERMINATION DEVICE

[76] Inventor: Van B. Philpot, Jr., P.O. Box 312, Houston, Miss. 38851

[21] Appl. No.: 679,647

[22] Filed: Apr. 23, 1976

Related U.S. Application Data

[63] Continuation-in-part of Ser. No. 579,871, May 22, 1975, Pat. No. 3,999,538.

[51] Int. Cl.² .............................................. A61B 5/02
[52] U.S. Cl. ...................... 128/2 G; 73/55; 128/2 F
[58] Field of Search ............... 128/2 F, 2 G, 2.05 D, 128/214 R, 214 A, 2, 2.05; 73/55

[56] References Cited

U.S. PATENT DOCUMENTS

| | | | |
|---|---|---|---|
| 2,600,324 | 6/1952 | Rappaport | 128/2.05 D |
| 2,866,453 | 12/1958 | Jewett | 128/2.05 D |
| 2,910,981 | 11/1959 | Wilson et al. | 128/214 A |
| 3,157,201 | 11/1964 | Littmann | 128/2.05 D |
| 3,610,228 | 10/1971 | Temkin | 128/2.05 D |
| 3,830,234 | 8/1974 | Kopp | 128/214 R |
| 3,834,372 | 9/1974 | Turney | 128/2 F |

OTHER PUBLICATIONS

Surgical Equipment, May–June, 1935, vol. 2, No. 3, p. 12.

*Primary Examiner*—Kyle L. Howell
*Attorney, Agent, or Firm*—Cushman, Darby & Cushman

[57] ABSTRACT

An apparatus for determining blood viscosity of blood in the body is disclosed. Venous pressure in a body vein is maintained at a constant pressure, blood is then withdrawn from the vein at a constant pressure for a period of time and the volume of blood withdrawn is determined to obtain an indication of blood viscosity when in the body. The time period may be constant and the blood volume is then inversely proportional to body blood viscosity. In another embodiment a predetermined volume of blood is withdrawn and the time period is measured which is directly proportional to blood viscosity in the body. The diagnostic apparatus comprises a hollow needle, a means for withdrawing and collecting blood from the vein through the hollow needle, a negative pressure measuring device such as a vacuum gauge for effectively measuring the negative pressure used to withdraw the blood and a timing device. The in vivo blood viscosity thus measured is directly proportional to the time required to withdraw a predetermined volume of blood and inversely proportional to the volume of blood withdrawn during a fixed time interval.

10 Claims, 6 Drawing Figures

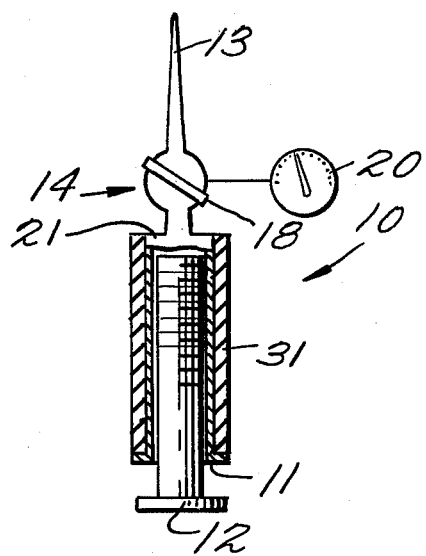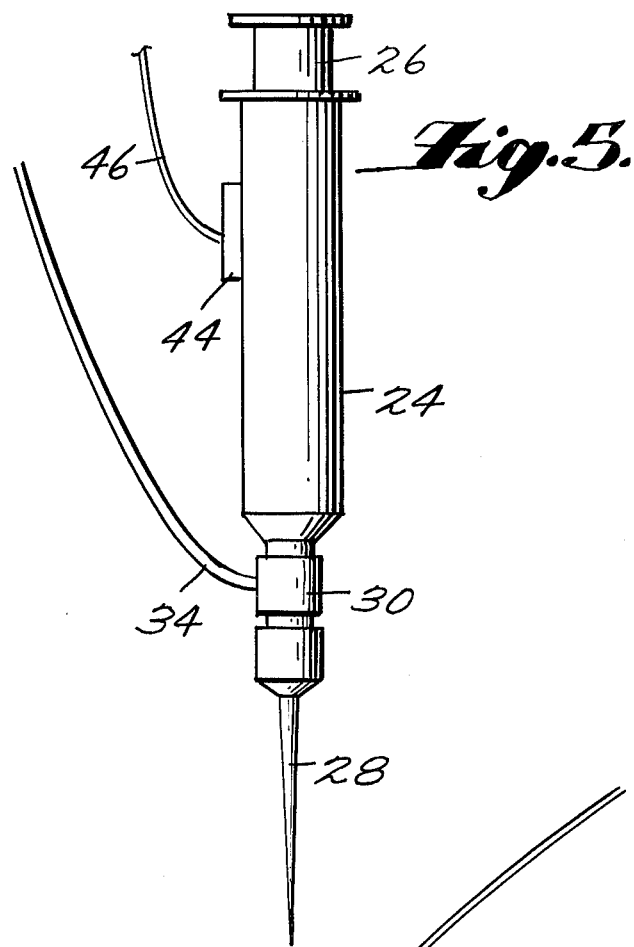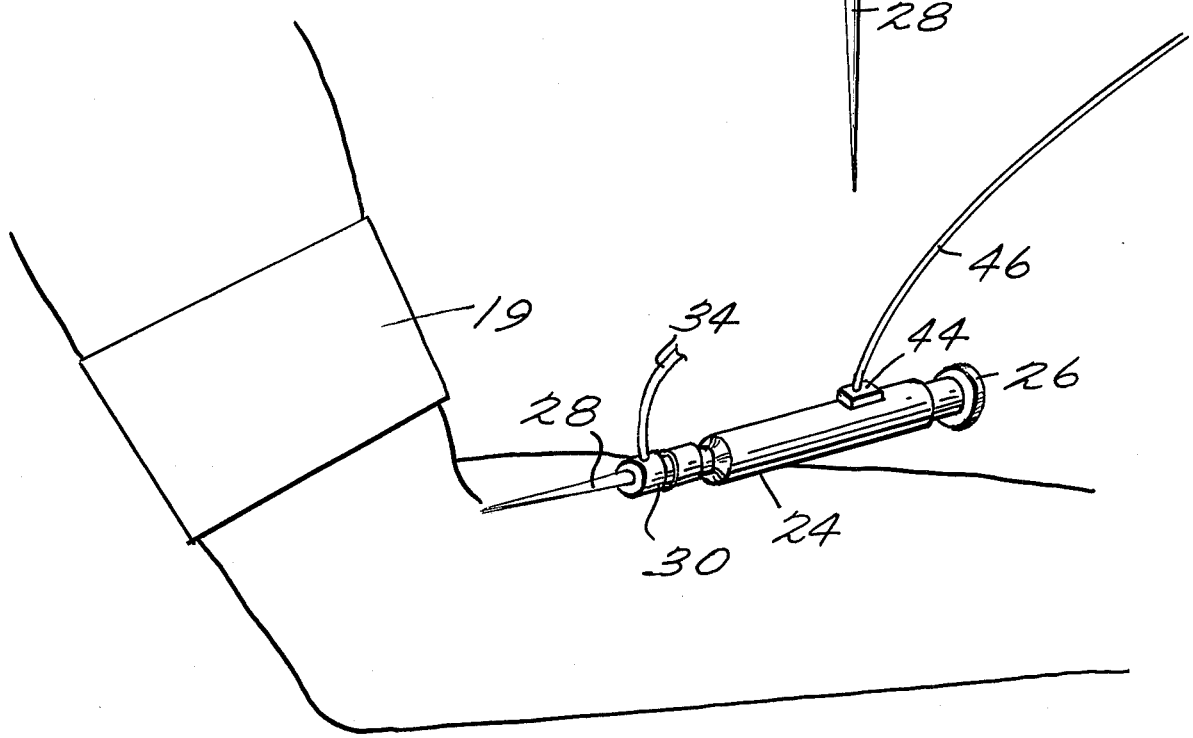

BLOOD VISCOSITY DETERMINATION DEVICE

CROSS-REFERENCE TO RELATED APPLICATIONS

This is a continuation-in-part of my copending application Ser. No. 579,871 filed May 22, 1975 now U.S. Pat. No. 3,999,538.

BACKGROUND OF THE INVENTION

It has now been found that the in vivo viscosity of blood varies among individuals, and that an in vivo viscosity measurement of blood substantially corresponding to the viscosity when in the body can be of value to the physicians in the diagnosis of certain body conditions. The present invention provides means for rapidly and inexpensively determining comparative substantially in vivo blood viscosity. The measurement of blood viscosity long after removal from the patient has been carried out in the past. However, viscosity of whole blood has not been studied thoroughly because of the difficulties in the settling of erythrocytes and of the very dramatic changes that occur in blood following its withdrawal from the cardiovascular system.

SUMMARY OF THE INVENTION

It is an important object of this invention to provide apparatus for determining in vivo blood viscosity rapidly and in an uncomplicated fashion.

Another object of this invention is to provide apparatus with which an in vivo blood viscosity determination can be carried out with simplified equipment without the need for highly trained personnel yet accurately indicates in vivo blood viscosity.

According to the invention, in vivo blood viscosity is determined by first maintaining constant venous pressure in a body vein. Blood is then withdrawn from the vein at a constant pressure for a predetermined time period with the volume of blood withdrawn acting as an indication of blood viscosity in the body.

In the preferred embodiment, venous pressure is maintained at a constant value with the aid of a blood pressure cuff set for example at 30 mm of mercury. Vena puncture is then made distal from the blood pressure cuff so that the venous pressure remains constant. The vena puncture is preferably carried out by a needle interconnected with a three-way stopcock, one passageway of which leads to a vacuum gauge and the other passage of which leads to a standard Luer syringe. By monitoring the vacuum gauge while retracting the plunger, a constant negative pressure can be maintained in the syringe for a predetermined period as for example 15 seconds. At the end of 15 seconds, the volume of blood withdrawn is measured. The variation in volume of blood is found to correspond to, and be inversely proportional to, blood viscosity of the blood in the body.

In an alternate procedure of this invention, the syringe plunger is retracted until a predetermined blood volume is extracted under a constant negative pressure and the time period necessary to withdraw that volume of blood is measured. That time period is proportional to the viscosity of the blood within the body.

A device for predetermining blood viscosity rapidly and inexpensively with uncomplicated equipment comprises a three passage valve or connector, a blood collecting body connected to one passage, a pressure monitoring device connected to a second passage and a needle connected to a third passage. Means for creating a vacuum in the blood collecting body enables one to draw blood into the blood collecting body under a predetermined negative pressure monitored by the pressure monitoring device.

Another embodiment of my invention includes a syringe needle, T-fitting and their tubing (all preferably disposable) fitted to a vacuum gauge which actuates an electronic timer thus requiring only one operator to withdraw the sample while the predetermined vacuum is maintained and the necessary timing is provided.

It is an advantage of this invention that the novel apparatus employed can be extremely inexpensive and the test can be carried out rapidly without the need for highly trained medical personnel. Tests of this type can be easily and conveniently carried out by technicians, such as medical laboratory technicians, without medical doctor supervision. The results obtained can be compared with standardized charts of, for example, volumes withdrawn in predetermined time periods under similar conditions with different groups of persons, such as persons who have myocardial infractions, healthy males, healthy females, men and women of predetermined ages and the like. The in vivo blood viscosity value so obtained is then compared to blood viscosity of various groups of individuals and diagnostic determinations and evaluations made.

BRIEF DESCRIPTION OF THE DRAWINGS

The above and other features of my invention will be better understood from a reading of the following specification in connection with the accompanying drawing in which;

FIG. 4 is a semi-diagrammatic illustration of another apparatus according to the invention;

FIG. 5 is a diagrammatic view of a modification of FIG. 3 using a fluid level transducer in association with the syringe barrel;

FIG. 6 is a perspective view of the syringe and needle device of FIG. 5 in the measuring position with respect to a subject's arm.

DESCRIPTION OF PREFERRED EMBODIMENTS

Figure 1:
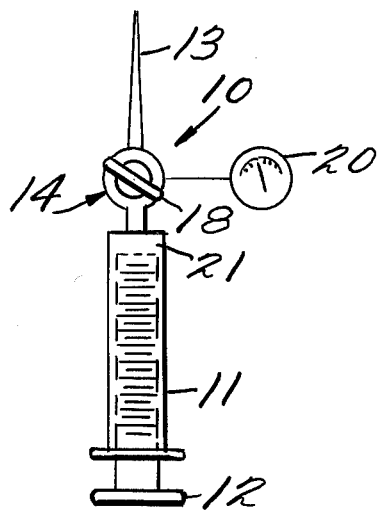
FIG. 1 is a semi-diagrammatic illustration of an apparatus in accordance with an embodiment of this invention.
Figure 2:
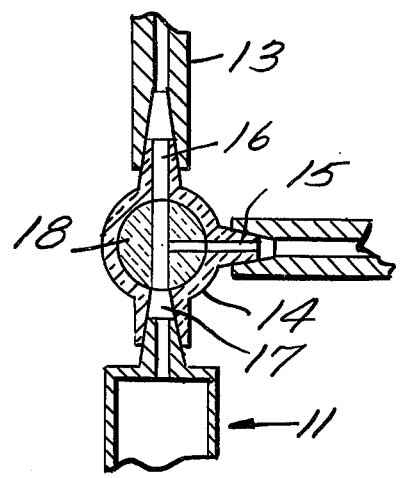
FIG. 2 is a cross-sectional view through a stopcock 14.

With reference now to the drawings and more particularly to FIG. 1, FIG. 2 and FIG. 4 an apparatus for determining blood viscosity is shown at 10. The apparatus comprises a substantially conventional syringe 11 having a plunger 12. The syringe can have a size of from 1 to 50 cc or larger. A conventional 20 gauge needle 13 is locked to a three-way stopcock 14 having a first passageway 16. A second passageway 15 is connected with a third passageway 17 leading to the syringe blood collecting body portion 21. Passageway 15 interconnects a conventional vacuum gauge 20 with the three passageways 15, 16 and 17. A shuttle 18 enables blocking of all three passageways 15, 16 and 17 and selective simultaneous interconnection of all three passageways when desired.

In a typical example of carrying out the method of this invention as illustrated in FIG. 6, where the blood volume withdrawn is the variable, a conventional blood pressure cuff 19 of a blood pressure manometer is applied to the arm about 2 inches above the subcubital arm vein of a human test subject. A pressure of 30 millimeters of mercury is maintained in an inflated blood pressure cuff. A vena puncture is performed distal from the cuff using the needle 13 which is a 1½ inch 20 gauge needle. The shuttle valve 18 allows all three passageways to be opened at once. The plunger 12 is withdrawn for a time of 15 seconds while monitoring the vacuum with the manometer or vacuum gauge 20 to maintain it at 3-10 inches of mercury, preferably 6 inches of mercury. The volume of blood removed is then measured by the calibrations on the syringe. This volume is indicative of and inversely proportional to the blood viscosity in vivo in the body from which the blood has been withdrawn. If the blood is thinner than a set standard, a greater volume will be withdrawn in the predetermined constant time period than if it is thicker than a set standard.

Figure 3:
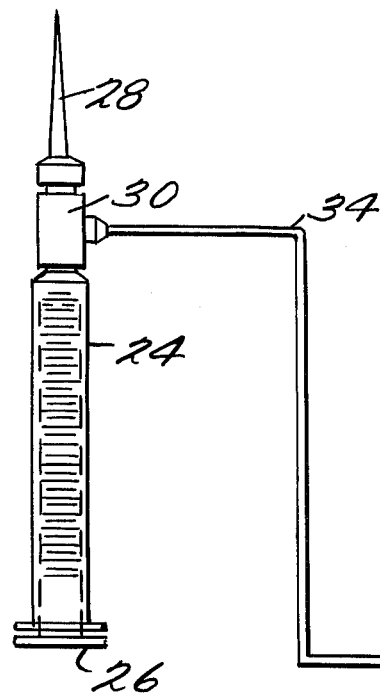
FIG. 3 is a diagrammatic view of another embodiment of the invention using an automated vacuum gauge, start control and electronic timer.
Figure 3:
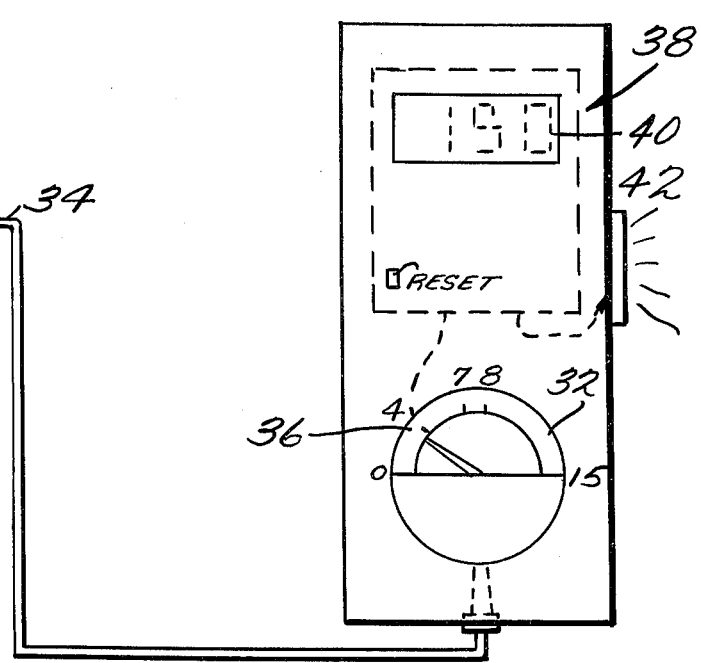

According to another embodiment of my invention as illustrated in FIGS. 3, 5 and 6 a syringe 24 calibrated up to 12-20 ml and preferably constructed of clear or translucent plastic is provided with a plunger 26, preferably of colored plastic to facilitate reading the calibrations on the syringe barrel. The barrel may be surrounded by a jacket 31 to regulate and to maintain a predetermined blood temperature in the syringe. A pressure measuring device or detector such as vacuum gauge 32 is preferably housed in common with an electronic clock or time measuring device 38 although it will be appreciated that a separate pressure sensitive electrical transducer might be employed if desired. A 20-gauge needle 28 is provided and a plastic "T" fitting 30 is located between the syringe barrel 24 and needle 28. The "T" fitting 30 has no valve means and is connected to vacuum gauge 32 via a thin tube 34. The plastic "T" fitting is provided with Luer locks on both ends and to the thin tubing 34.

The vacuum gauge 32 provides a visual pressure monitor to the operator of the apparatus for helping him to maintain a constant negative withdrawal pressure. The gauge 32 is also fitted with an electrical switch 36 or other transducer which, when a predetermined negative pressure is reached (as caused by withdrawing the plunger in the syringe) electrically actuates an electronic timer 38 having a digital elapsed time display 40. When a predetermined programmed time period is reached, say 15 seconds, the electronic timer 38 gives a signal such as an audible sound from Sonalert 42, flashing light (not shown) or the like thereby signalling the operator to stop the withdrawal process.

The switch 36 may, for example, simply take the form of an electrical contact completed by the gauge needle whenever above a preset level or it could be a more sophisticated light sensitive switch dependent upon needle movement or it could be a pressure sensitive electrical switch transducer directly responding to the negative pressure in line 34 as will be appreciated.

The syringe, T-fitting, needle and thin tube are all preferably of the single use, disposable type and are conveniently connected together via Luer locks, to the vacuum gauge/electronic timer assembly.

The vacuum gauge is of conventional pressure gauge design provided with a very sensitive pressure switch (available from Edmund Scientific Co.) positioned such that when the vacuum reaches a predetermined level, about 4 inches of mercury as shown in the figure, the electronic timer 38 is activated. As will be appreciated, other forms of pressure sensitive electrical transducer could also be used for activating the electric timer when a predetermined negative pressure is detected. Further, other forms of pressure monitors (i.e., an electronic pressure gauge) could be utilized for monitoring and/or controlling the desired substantially constant negative pressure during the blood withdrawal process. Preferably the vacuum gauge has a display of 180° and is graduated in units of vacuum ranging from 0 to 15 inches of mercury. The timer remains activated by switch 36 as long as at least the preset minimum vacuum is maintained.

The electronic timer 38 may be realized from commercially available digital stop watches, for instance the Heathkit digital stopwatch model GB-1201 to commence counting in seconds, once triggered, up to a prefixed time, say 15 seconds, when a signalling device is actuated indicating the operator to stop withdrawal of blood.

This electrical stopwatch is already provided with electrical input terminals for starting the measurement of elapsed time. A programmable second counter is also provided which may be preset to represent a desired time interval, for example, 15 seconds, which is compared to the time measuring counter and provides an electrical "alarm" signal at output terminals when that preset time is attained. Thus no electrical modification of this stopwatch circuitry is actually required although it is preferred to eliminate unnecessary components (e.g., hour and minute timing circuitry, unused switches, jacks and terminals, etc.) when building the timer into a common housing with the vacuum gauge as in the preferred exemplary embodiment of this invention.

In operation using the above-described vacuum gauge and automatic timing start control, a conventional blood cuff is applied to the subject's arm about 2 inches above the subcubital arm vein; a pressure of about 30 mm of mercury is maintained in the inflated pressure cuff. A vena puncture is performed distal from the cuff using needle 28, which is a 1½ inch 20 gauge needle. Plunger 26 is withdrawn from the barrel 24 causing a pressure drop in the thin tube 34 and actuating the pressure switch 36 when 4 inches of vacuum is attained which, in turn, starts the electronic timer 38. The timer continues to count in seconds, provided that at least the preset desired vacuum is maintained, until a predetermined time interval is reached, for instance 15 seconds. At that point an audible alarm 42 is sounded which emits a sharp beep and all operations stop.

The volume of blood thus withdrawn at the fixed time and vacuum is then related to the blood viscosity. Using this type of apparatus the withdrawal of blood actuates the timer and once the proper vacuum is reached, the operator is free to use both hands in withdrawing the sample thus simplifying the overall precedure and permitting a single operator to accurately perform the procedure.

The alternative viscosity measurement may also be realized by employing an apparatus similar to that shown in FIG. 3 for automatically starting the electronic timer as shown in FIG. 5 and further providing a suitable fluid level sensor/electrical transducer 44 in association with and connected via line 46 to the blood collection body to automatically stop the timer 38 after collection of a preset desired volume of blood. The electronic stopwatch previously referenced is also provided with electrical input terminals for stopping its operation.

It has been found that the blood viscosity of different groups of human subjects varies greatly. Thus a comparative measurement at predetermined conditions on a large groups of individuals can enable useful diagnostic information to be obtained on a single sample by comparison of that sample with charts, graphs and standards of comparison previously made under similar conditions.

The values of the table below were obtained using the method of the above diagnostic procedure. As seen in the table, a total of six volunteer normal female subjects were used, and the average amount of blood withdrawn was 8.9 ml. A total of eight adult male subjects were used and the average amount of withdrawn blood was 7.2 ml. After exercise, the amount of blood withdrawn from one of the male volunteers increased from 7.0 ml to 7.4 ml and in a second volunteer male, the amount of blood withdrawn after exercise increased from 7.0 ml to 8.0 ml, indicating a decrease in blood viscosity following exercise. Results of this particular test from patients with myocardial infarction shows a significant decrease in the amount of blood withdrawn by this method. The average amount of blood drawn from two females with myocardial infarction was 7.0 ml in contrast to a normal level of 8.9 ml. The average of two male patients with myocardial infarction was 4.1 ml in contrast to a normal average in males of 7.2 ml.

| AMOUNT OF BLOOD IN MILLIMETERS WITHDRAWN FROM VENIPUNCTURE AT 6 IN. VACUUM FOR 15 SECONDS ||||| 
|---|---|---|---|---|
| Normal Volunteers Basal Conditions || Normal volunteers After Exercise | Patients with Myocardial Infarction ||
| Female | Male | Male | Female | Male |
| 9.10 | 7.0 |  | 6.2 | 4.6 |
| 8.90 | 8.0 |  | 7.8 | 3.5 |
| 9.00 | 7.0 | 7.4 |  |  |
| 8.90 | 7.3 |  |  |  |
| 8.80 | 7.0 | 8.0 |  |  |
| 8.90 | 7.5 |  |  |  |
|  | 7.1 |  |  |  |
|  | 7.1 |  |  |  |
| Average: |  |  |  |  |
| 8.9 | 7.2 | 7.7 | 7 | 4.1 |
| 53:60 = 8:93 |  | 58:00 = 7:25 | 14: = 7 | 8:10 = 4:05 |

In another embodiment of this invention this method was duplicated except that the syringe was withdrawn to remove a predetermined volume of blood, as for example 30 ml. and the time of withdrawal of blood was measured rather than being a constant. The amount of time required to remove a predetermined constant volume of blood is then the variable which is proportional to blood viscosity. Similar charts can be obtained based on time variations, rather than volume variations, if desired. It has been found that volume variations provide a simpler and more effective means of determining blood viscosity on a comparative basis than time variations.

While the above described exemplary apparatus embodiments are preferred for usage in the present invention, various apparatus modifications may be made within the scope of this invention. In some cases, the manometer or other pressure gauge measurement can be incorporated directly in the blood collecting body rather than being attached through a three-way valve or connection. In other cases it may be desirable to provide a water jacket surrounding the syringe to maintain a constant temperature about the blood collecting chamber. This would provide some greater degree of accuracy although as a practical matter at the ambient temperatures normally encountered, the blood remains substantially at body temperature throughout the viscosity measurement in accordance with this invention. On balance temperature variations in the diagnostic device are of little significance.

In all cases, it is preferred to maintain a constant venous pressure during withdrawal and measurement of the blood, and to maintain and withdraw the blood under a constant negative pressure. Preferably the venous pressure applied by the cuff is in the range of from 10 mm to 70 mm of mercury, the negative pressure applied by the plunger is in the range of from 1 inch to 20 inches, and the time of withdrawal is in the range of from 5 seconds to 60 seconds. Preferably, various charts and graphs and standards of comparison are established for comparison of a subject's blood volume withdrawn which is withdrawn in predetermined time constant periods, at predetermined constant negative pressure through predetermined constant needle sizes at substantially ambient temperatures and preferably in the range of from 65° to 80° F. Alternately such charts are based on comparisons of time of withdrawal with constant volumes withdrawn. The viscosity measurement is made within seconds of withdrawal of blood from the body thus avoiding viscosity changes due to settling of blood components as well as other dramatic physical and chemical changes which are known to occur in blood with the passage of time after removal from the body.

Blood viscosity measurements made according to the method and using the apparatus of my invention are useful diagnostic aids to the physician. For example, it has been observed that during the acute phase of myocardial infarction, i.e., onset up to 24–48 hours thereafter, blood viscosity of the patient decreases. This lends support to that body of opinion that anticoagulant thereby is not indicated at that time. However, patients who have previously suffered a myocardial infarction at a later point in time tend to exhibit higher blood viscosity values than normal levels, indicating drug therapy or the like, such as anti-coagulants, to reduce the viscosity to a more normal level.

As the blood viscosity value determined is essentially a parameter of the change in the blood, expressed on a continuum from the liquid to the solid phase, it is envisioned that a patient's blood viscosity is of value in indicating a change in the blood toward the solid phase and predicting consequential results in the cardiovascular system.

Using the apparatus and methods described above quick, safe and accurate measurements of blood viscosity are possible by the clinician, or a member of his staff, and the results are readily available for diagnostic purposes. Further, the volume of blood withdrawn need not be discarded but may be used for other blood testing operations customarily made, such as a complete blood count (CBC), blood urea nitrogen (BUN), serology and the like.

I claim:

1. Diagnostic apparatus for determining in vivo the whole blood viscosity of blood in the vein of a subject animal while the venous blood pressure in at least a portion of said vein is maintained substantially constant, said diagnostic apparatus comprising:

a hollow needle having a pointed end for in vivo communication with said whole blood through puncture of said portion of said vein, blood withdrawing means including means for collecting the blood withdrawn from said vein through said hollow needle and for quantitatively measuring the volume of said withdrawn and collected blood, said blood withdrawing means communicated to said hollow needle at an end distal from said pointed end and adapted to establish a negative pressure thereat with respect to said venous pressure thereby drawing said in vivo blood through the hollow needle;

a negative pressure measuring means communicated to said distal end of the hollow needle for indicating the negative pressure in the region thereof as the blood is being withdrawn through said hollow needle;

said blood withdrawing means also including means for controlling said negative pressure in accordance with said negative pressure measuring means so as to establish a predetermined substantially constant fluid pressure drop across the hollow needle;

timing means for measuring elapsed time from a starting signal; and automatic actuation means connected to automatically provide said starting time signal to said timing means when said negative pressure reaches a predetermined preset magnitude;

whereby the in vivo blood viscosity is directly proportional to the time required to withdraw a predetermined quantity of blood and inversely proportional to the volume of blood withdrawn during a predetermined time interval.

2. The diagnostic apparatus of claim 1 wherein said blood withdrawing means comprises a volumetrically calibrated syringe.

3. The diagnostic apparatus of claim 1 wherein said negative pressure measuring means comprises a vacuum gauge.

4. The diagnostic apparatus of claim 1 further including means disposed about said means for collecting blood for regulating and maintaining the temperature of the blood contained therein within a predetermined temperature range.

5. The diagnostic apparatus of claim 1 wherein said timing means includes means for providing an output signal after measuring a predetermined preset elapsed time and further comprising humanly sensible output means connected to provide a visual, audible a both visual and audible output indication in response to said output signal.

6. The diagnostic apparatus of claim 1 wherein said timing means comprises an electronic stopwatch.

7. The diagnostic apparatus of claim 1 wherein said automatic actuation means comprises a pressure sensitive switch.

8. The diagnostic apparatus of claim 1 wherein said automatic actuation means comprises an electrical switch coupled to said negative pressure measuring means so as to be actuated when the measured negative pressure exceeds a predetermined preset magnitude.

9. The diagnostic apparatus of claim 1 further comprising automatic stop means adapted to monitor the volume of collected blood and connected to automatically stop the operation of said timing means when a predetermined preset volume of blood has been collected.

10. Diagnostic apparatus for determining in vivo the whole blood viscosity of blood in the vein of a subject animal while the venous blood pressure in at least a portion of said vein is maintained substantially constant, said diagnostic apparatus comprising:

a hollow needle having a pointed end for in vivo connection with said whole blood through puncture of said portion of said vein;

blood withdrawing means including means for collecting the blood withdrawn from said vein through said hollow needle and for quantitatively measuring the volume of such withdrawn and collected blood, said blood withdrawing means connected to said hollow needle at an end distal from said pointed end and adapted to establish a negative pressure thereat with respect to said venous pressure thereby withdrawing said in vivo blood through the hollow needle;

a negative pressure measuring means connected to said distal end of the hollow needle for indicating the negative pressure in the region thereof as the blood is being withdrawn through said hollow needle;

said blood withdrawing means also including means for controlling said negative pressure in accordance with said negative pressure measuring means so as to establish a predetermined, substantially constant negative pressure drop across the hollow needle;

timing means for measuring elapsed time from a starting time signal;

automatic actuation means connected to automatically provide said starting time signal to said timing means when said predetermined negative pressure is established;

said timing means providing an output signal after measuring a predetermined preset elapsed time;

wherein the in vivo blood viscosity is directly proportional to the time required to withdraw a predetermined quantity of blood and inversely proportional to the volume of blood withdrawn during a predetermined time interval.

* * * * *